United States Patent
Luo

(12) 
(10) Patent No.: US 6,433,237 B1
(45) Date of Patent: Aug. 13, 2002

(54) IRON-BASED CATALYST COMPOSITION FOR PRODUCING OLIGOMERS OF CONJUGATED DIENES

(75) Inventor: Steven Luo, Akron, OH (US)

(73) Assignee: Bridgestone Corporation, Tokyo (JP)

(*) Notice: Subject to any disclaimer, the term of this patent is extended or adjusted under 35 U.S.C. 154(b) by 0 days.

(21) Appl. No.: 09/788,800

(22) Filed: Feb. 19, 2001

(51) Int. Cl.$^7$ .............. C07C 2/40; B01J 3/12; B01J 31/14; C08F 4/14

(52) U.S. Cl. ............ 585/507; 585/506; 585/509; 502/102; 502/152; 502/153; 502/154; 502/155; 502/158; 502/162; 526/90; 526/95; 526/100; 526/126; 526/127; 526/128; 526/135; 526/136; 526/142; 526/143; 526/144; 526/171; 526/183; 526/193; 526/233; 526/237

(58) Field of Search ............ 502/102, 152, 502/153, 154, 155, 158, 162; 526/90, 95, 100, 126, 127, 128, 135, 136, 142, 143, 144, 171, 183, 193, 233, 237; 585/506, 507, 509

(56) References Cited

U.S. PATENT DOCUMENTS

| | | | |
|---|---|---|---|
| 3,419,505 A | 12/1968 | Marsico | |
| 3,457,186 A | 7/1969 | Marsico | |
| 3,498,963 A | 3/1970 | Ichikawa et al. | |
| 3,725,373 A | 4/1973 | Yoo | |
| 3,778,424 A | 12/1973 | Sugiura et al. | |
| 3,957,894 A | 5/1976 | Saeki et al. | |
| 4,048,418 A | 9/1977 | Throckmorton | 526/138 |
| 4,148,983 A | 4/1979 | Throckmorton et al. | 526/139 |
| 4,168,357 A | 9/1979 | Throckmorton et al. | 526/139 |
| 4,168,374 A | 9/1979 | Throckmorton et al. | 526/139 |
| 4,182,813 A | 1/1980 | Makino et al. | 526/92 |
| 4,379,898 A | 4/1983 | Ashitaka et al. | 525/247 |
| 4,645,809 A | 2/1987 | Bell | 526/140 |
| 4,751,275 A | 6/1988 | Witte et al. | 526/139 |
| 5,239,023 A | 8/1993 | Hsu et al. | 526/141 |
| 5,283,294 A | 2/1994 | Hsu et al. | 525/247 |
| 5,356,997 A | 10/1994 | Massie, II et al. | 525/237 |
| 5,677,405 A | 10/1997 | Goodall et al. | 526/281 |
| 5,891,963 A | 4/1999 | Brookhart et al. | 525/326.1 |
| 5,919,875 A | 7/1999 | Luo et al. | 526/139 |
| 6,127,301 A * | 10/2000 | Iwanaga et al. | 502/119 |
| 6,160,063 A | 12/2000 | Luo | 526/139 |
| 6,180,734 B1 | 1/2001 | Luo | 526/139 |
| 6,320,004 B1 * | 11/2001 | Luo | 502/152 |

FOREIGN PATENT DOCUMENTS

| | | |
|---|---|---|
| EP | 0 994 128 A1 | 4/2000 |
| EP | 0 994 129 A1 | 4/2000 |

OTHER PUBLICATIONS

English Abstract of Japanese Patent No. 48–6939. (1970) No month.
English Abstract of Japanese Patent No. 48/64178 (1971) No month.
English Abstract of Japanese Patent No. 45011154 (1970) No month.
"π–Allymetal Derivatives in Organic Synthesis" by R. Baker, *Chemical Review*, vol. 73, pp. 487–496, (1973) No month.
"the Oligomerization of Butadiene with an Iron Complex Catalyst" by Hidai et al., *Bulletin of Chemical Society of Japan*, vol. 38, pp. 1243–1247 (1965) No month.
"The Oligomerization of Butadiene with an Iron Complex Catalysts. II. The Effects of Additives" by Hidai et al., *Bulletin of Chemical Society of Japan*, vol. 39, pp. 1357–1364 (1966) No month.
"Linear Dimerization of Butadiene with Ferric Chloride–t–riphenylphosphine–Triethylaluminum Catalyst" by Takahashi et al., *Journal of Organic Chemistry*, vol. 30, pp. 1661–1662 (1965) No month.
Syndiotactic 1,2–Polybutadiene with Co–$CS_2$ Catalyst System I. Preparation Properties and Application of Highly Crystalline Syndiotactic 1,2–Polybutadiene, II. Catalyst for Stereospecific Polymerization of Butadiene to Syndiotactic 1,2–Polybutadiene, III. $^1H$ and $^{13}C$–NMR Study of Highly Syndiotactic 1,2–Polybutadiene and IV Mechanism of Syndiotactic Polymerization of Butadiene with Cobalt Compounds–Organoaluminum–$CS_2$, *Journal of Polymer Science: Polymer Chemistry Edition*, by H. Ashitaka et al., vol. 21, pp. 1853–1860 and 1951–1995, (1983) No month.
Comprehensive Polymer Science, by Porri and Giarrusso, Pergamon Press, Oxford, vol. 4, p. 53, (1989) No month.

* cited by examiner

*Primary Examiner*—Elizabeth D. Wood
(74) *Attorney, Agent, or Firm*—David G. Burleson; Arthur M. Reginelli

(57) ABSTRACT

A catalyst composition that is the combination of or the reaction product of ingredients comprising (a) (i) a halogen-containing iron compound or (ii) an iron-containing compound and a halogen-containing compound, (b) a silyl phosphonate, and (c) an organoaluminum compound.

20 Claims, No Drawings

IRON-BASED CATALYST COMPOSITION FOR PRODUCING OLIGOMERS OF CONJUGATED DIENES

FIELD OF THE INVENTION

This invention relates to an iron-based catalyst composition for producing oligomers of conjugated dienes.

BACKGROUND OF THE INVENTION

Conjugated dienes such as 1,3-butadiene and isoprene undergo a variety of catalytic oligomerization reactions to give cyclic or acyclic oligomers. These oligomers are valuable feedstocks for producing fine organic chemicals. For example, the dimers and trimers are utilized as intermediates for synthesizing plasticizers, flame retardants, terpenoid and sesquiterpenoid compounds of biological interest, and fragrances.

Various coordination catalyst systems based on nickel, palladium, cobalt, titanium, chromium, and iron have been reported for catalyzing the oligomerization of conjugated dienes. The majority of these catalyst systems, however, have no practical utility, because they have low activity and poor selectivity. The resulting oligomerization product is often a complicated mixture of cyclic and acyclic dimers, trimers, tetramers, and higher oligomers. Furthermore, some oligomerization catalyst systems also generate a certain amount of polymer in the oligomerization product mixtures.

Several iron-based coordination catalyst systems for oligomerizing conjugated dienes are known. For example, one process for the oligomerization of 1,3-butadiene employs a catalyst system comprising iron(III) acetylacetonate and triethylaluminum. Another process employs a catalyst system comprising iron(III) acetylacetonate, triethylaluminum, and triphenylphosphine. Yet another process employs a catalyst system comprising iron(III) chloride, triphenylphosphine, and triethylaluminum. All of these iron-based catalyst systems, however, have very low activity and poor selectivity, and the resulting oligomerization product is a mixture of cyclic and acyclic dimers, trimers, and higher oligomers, as well as polymer.

Because the oligomers of conjugated dienes are useful products and the catalyst systems known heretofore have many shortcomings, it would be advantageous to develop a new catalyst system that has high activity and selectivity for preparing oligomers of conjugated dienes.

SUMMARY OF THE INVENTION

In general the present invention provides a catalyst composition that is the combination of or the reaction product of ingredients comprising (a) (i) a halogen-containing iron compound or (ii) an iron-containing compound and a halogen-containing compound, (b) a silyl phosphonate, and (c) an organoaluminum compound.

The present invention also includes a catalyst composition formed by a process comprising the steps of combining (a) (i) a halogen-containing iron compound or (ii) an iron-containing compound and a halogen-containing compound, (b) a silyl phosphonate, and (c) an organoaluminum compound.

The present invention further includes a process for forming conjugated diene oligomers comprising the step of oligomerizing conjugated diene monomers in the presence of a catalytically effective amount of a catalyst composition formed by combining (a) (i) a halogen-containing iron compound or (ii) an iron-containing compound and a halogen-containing compound, (b) a silyl phosphonate, and (c) an organoaluminum compound.

Advantageously, the catalyst composition of this invention has very high activity, which allows conjugated diene oligomers to be produced in very high yields with low catalyst levels after relatively short oligomerization times. In addition, since this catalyst composition is highly active even at low temperatures, the oligomerization may be carried out under very mild temperature conditions, thereby avoiding thermal polymerization and/or cracking or other deleterious effects. Further, the iron compounds that are utilized are generally stable, inexpensive, relatively innocuous, and readily available. Furthermore, this catalyst composition is very selective. For instance, by utilizing this catalyst, 1,3-butadiene can be converted quantitatively to acyclic dimers without the production of any other products.

DETAILED DESCRIPTION OF ILLUSTRATIVE EMBODIMENTS

The catalyst composition is formed by combining (a) (i) a halogen-containing iron compound or (ii) an iron-containing compound and a halogen-containing compound, (b) a silyl phosphonate, and (c) an organoaluminum compound. In addition to these catalyst ingredients (a), (b), and (c), other organometallic compounds or Lewis bases that are known in the art can also be added, if desired.

In one embodiment, where a halogen-containing iron compound is used as ingredient (a), various halogen-containing iron compounds or mixtures thereof can be employed. The iron atom in the halogen-containing iron compounds can be in various oxidation states including, but not limited to, the +2, +3, and +4 oxidation states. Divalent iron compounds (also called ferrous compounds), where the iron atom is in the +2 oxidation state, and trivalent iron compounds (also called ferric compounds), where the iron atom is in the +3 oxidation state, are preferred.

Suitable halogen-containing iron compounds that can be utilized include, but are not limited to, iron fluorides, iron chlorides, iron bromides, iron iodides, iron oxyhalides, and mixtures thereof. Some specific examples of halogen-containing iron compounds include iron(II) fluoride, iron(III) fluoride, iron(III) oxyfluoride, iron(II) chloride, iron(III) chloride, iron(III) oxychloride, iron(II) bromide, iron(III) bromide, iron (III) oxybromide, and iron(II) iodide.

In a second embodiment, where an iron-containing compound and a halide-containing compound are used as ingredient (a), various iron-containing compounds or mixtures thereof can be employed.

Preferably, iron-containing compounds that are soluble in a hydrocarbon solvent such as aromatic hydrocarbons, aliphatic hydrocarbons, or cycloaliphatic hydrocarbons are employed. Hydrocarbon-insoluble iron-containing compounds, however, can be suspended in the oligomerization medium to form the catalytically active species and are therefore useful.

The iron atom in the iron-containing compounds can be in various oxidation states including, but not limited to, the 0, +2, +3, and +4 oxidation states. Divalent iron compounds and trivalent iron compounds are preferred. Suitable iron-containing compounds that can be utilized include, but are not limited to, iron carboxylates, iron organophosphates, iron organophosphonates, iron organophosphinates, iron carbamates, iron dithiocarbamates, iron xanthates, iron β-diketonates, iron alkoxides or aryloxides, organoiron compounds, and mixtures thereof.

Suitable iron carboxylates include iron(II) formate, iron (III) formate, iron(II) acetate, iron(III) acetate, iron(II)

acrylate, iron(III) acrylate, iron(II) methacrylate, iron(III) methacrylate, iron(II) valerate, iron(III) valerate, iron(II) gluconate, iron(III) gluconate, iron(II) citrate, iron(III) citrate, iron(II) fumarate, iron(III) fumarate, iron(II) lactate, iron(III) lactate, iron(II) maleate, iron(III) maleate, iron(II) oxalate, iron(III) oxalate, iron(II) 2-ethylhexanoate, iron(III) 2-ethylhexanoate, iron(II) neodecanoate, iron(III) neodecanoate, iron(II) naphthenate, iron(III) naphthenate, iron(II) stearate, iron(III) stearate, iron(II) oleate, iron(III) oleate, iron(II) benzoate, iron(III) benzoate, iron(II) picolinate, and iron(III) picolinate.

Suitable iron organophosphates include iron(II) dibutyl phosphate, iron(III) dibutyl phosphate, iron(II) dipentyl phosphate, iron(III) dipentyl phosphate, iron(II) dihexyl phosphate, iron(III) dihexyl phosphate, iron(II) diheptyl phosphate, iron (III) diheptyl phosphate, iron (II) dioctyl phosphate, iron(III) dioctyl phosphate, iron(II) bis(1-methylheptyl) phosphate, iron(III) bis(1-methylheptyl) phosphate, iron(II) bis(2-ethylhexyl) phosphate, iron(III) bis(2-ethylhexyl) phosphate, iron(II) didecyl phosphate, iron (III) didecyl phosphate, iron(II) didodecyl phosphate, iron (III) didodecyl phosphate, iron(II) dioctadecyl phosphate, iron(III) dioctadecyl phosphate, iron(II) dioleyl phosphate, iron(III) dioleyl phosphate, iron(II) diphenyl phosphate, iron(III) diphenyl phosphate, iron(II) bis(p-nonylphenyl) phosphate, iron(III) bis(p-nonylphenyl) phosphate, iron(II) butyl (2-ethylhexyl) phosphate, iron(III) butyl (2-ethylhexyl) phosphate, iron(II) (1-methylheptyl) (2-ethylhexyl) phosphate, iron(III) (1-methylheptyl) (2-ethylhexyl) phosphate, iron(II) (2-ethylhexyl) (p-nonylphenyl) phosphate, and iron(III) (2-ethylhexyl) (p-nonylphenyl) phosphate.

Suitable iron organophosphonates include iron(II) butyl phosphonate, iron(III) butyl phosphonate, iron(II) pentyl phosphonate, iron(III) pentyl phosphonate, iron(II) hexyl phosphonate, iron(III) hexyl phosphonate, iron(II) heptyl phosphonate, iron(III) heptyl phosphonate, iron(II) octyl phosphonate, iron(III) octyl phosphonate, iron(II) (1-methylheptyl) phosphonate, iron(III) (1-methylheptyl) phosphonate, iron(II) (2-ethylhexyl) phosphonate, iron(III) (2-ethylhexyl) phosphonate, iron(II) decyl phosphonate, iron(III) decyl phosphonate, iron(II) dodecyl phosphonate, iron(III) dodecyl phosphonate, iron(II) octadecyl phosphonate, iron(III) octadecyl phosphonate, iron(II) oleyl phosphonate, iron(III) oleyl phosphonate, iron(II) phenyl phosphonate, iron(III) phenyl phosphonate, iron(II) (p-nonylphenyl) phosphonate, iron(III) (p-nonylphenyl) phosphonate, iron(II) butyl butylphosphonate, iron(III) butyl butylphosphonate, iron(II) pentyl pentylphosphonate, iron (III) pentyl pentylphosphonate, iron(II) hexyl hexylphosphonate, iron(III) hexyl hexylphosphonate, iron (II) heptyl heptylphosphonate, iron(III) heptyl heptylphosphonate, iron(II) octyl octylphosphonate, iron (III) octyl octylphosphonate, iron(II) (1-methylheptyl) (1-methylheptyl)phosphonate, iron(III) (1-methylheptyl) (1-methylheptyl)phosphonate, iron(II) (2-ethylhexyl) (2-ethylhexyl)phosphonate, iron(III) (2-ethylhexyl) (2-ethylhexyl)phosphonate, iron(II) decyl decylphosphonate, iron(III) decyl decylphosphonate, iron (II) dodecyl dodecylphosphonate, iron(III) dodecyl dodecylphosphonate, iron(II) octadecyl octadecylphosphonate, iron(III) octadecyl octadecylphosphonate, iron(II) oleyl oleylphosphonate, iron (III) oleyl oleylphosphonate, iron(II) phenyl phenylphosphonate, iron (III) phenyl phenylphosphonate, iron(II) (p-nonylphenyl) (p-nonylphenyl)phosphonate, iron (III) (p-nonylphenyl) (p-nonylphenyl)phosphonate, iron(II) butyl (2-ethylhexyl)phosphonate, iron(III) butyl (2-ethylhexyl)phosphonate, iron(II) (2-ethylhexyl) butylphosphonate, iron(III) (2-ethylhexyl) butylphosphonate, iron(II) (1-methylheptyl) (2-ethylhexyl) phosphonate, iron(III) (1-methylheptyl) (2-ethylhexyl) phosphonate, iron(II) (2-ethylhexyl) (1-methylheptyl) phosphonate, iron(III) (2-ethylhexyl) (1-methylheptyl) phosphonate, iron(II) (2-ethylhexyl) (p-nonylphenyl) phosphonate, iron(III) (2-ethylhexyl) (p-nonylphenyl) phosphonate, iron(II) (p-nonylphenyl) (2-ethylhexyl) phosphonate, and iron (III) (p-nonylphenyl) (2-ethylhexyl) phosphonate.

Suitable iron organophosphinates include iron(II) butylphosphinate, iron(III) butylphosphinate, iron(II) pentylphosphinate, iron(III) pentylphosphinate, iron(II) hexylphosphinate, iron(III) hexylphosphinate, iron(II) heptylphosphinate, iron(III) heptylphosphinate, iron(II) octylphosphinate, iron(III) octylphosphinate, iron(II) (1-methylheptyl)phosphinate, iron(III) (1-methylheptyl) phosphinate, iron(II) (2-ethylhexyl)phosphinate, iron(III) (2-ethylhexyl)phosphinate, iron(II) decylphosphinate, iron (III) decylphosphinate, iron(II) dodecylphosphinate, iron (III) dodecylphosphinate, iron(II) octadecylphosphinate, iron(III) octadecylphosphinate, iron(II) oleylphosphinate, iron(III) oleylphosphinate, iron(II) phenylphosphinate, iron (III) phenylphosphinate, iron(II) (p-nonylphenyl) phosphinate, iron(III) (p-nonylphenyl)phosphinate, iron(II) dibutylphosphinate, iron(III) dibutylphosphinate, iron(II) dipentylphosphinate, iron(III) dipentylphosphinate, iron(II) dihexylphosphinate, iron(III) dihexylphosphinate, iron(II) diheptylphosphinate, iron(III) diheptylphosphinate, iron(II) dioctylphosphinate, iron(III) dioctylphosphinate, iron(II) bis (1-methylheptyl)phosphinate, iron (III) bis(1-methyheptyl) phosphinate, iron(II) bis (2-ethylhexyl)phosphinate, iron (III) bis(2-ethylhexyl)phosphinate, iron(II) didecylphosphinate, iron(III) didecylphosphinate, iron(II) didodecylphosphinate, iron(III) didodecylphosphinate, iron (II) dioctadecylphosphinate, iron(III) dioctadecylphosphinate, iron(II) dioleylphosphinate, iron (III) dioleylphosphinate, iron(II) diphenylphosphinate, iron (III) diphenylphosphinate, iron(II) bis(p-nonylphenyl) phosphinate, iron (III) bis (p-nonylphenyl) phosphinate, iron (II) butyl(2-ethylhexyl)phosphinate, iron(III) butyl(2-ethylhexyl)phosphinate, iron(II) (1-methylheptyl) (2-ethylhexyl) phosphinate, iron (III) (1-methylheptyl) (2-ethylhexyl)phosphinate, iron(II) (2-ethylhexyl)(p-nonylphenyl)phosphinate, and iron(III) (2-ethylhexyl)(p-nonylphenyl)phosphinate.

Suitable iron carbamates include iron(II) dimethylcarbamate, iron(III) dimethylcarbamate, iron(II) diethylcarbamate, iron(III) diethylcarbamate, iron(II) diisopropylcarbamate, iron(III) diisopropylcarbamate, iron (II) dibutylcarbamate, iron(III) dibutylcarbamate, iron(II) dibenzylcarbamate, and iron(III) dibenzylcarbamate.

Suitable iron dithiocarbamates include iron (II) dimethyldithiocarbamate, iron(III) dimethyldithiocarbamate, iron(II) diethyldithiocarbamate, iron(III) diethyldithiocarbamate, iron(II) diisopropyldithiocarbamate, iron(III) diisopropyldithiocarbamate, iron(II) dibutyldithiocarbamate, iron(III) dibutyldithiocarbamate, iron(II) dibenzyldithiocarbamate, and iron(III) dibenzyldithiocarbamate.

Suitable iron xanthates include iron(II) methylxanthate, iron(III) methylxanthate, iron(II) ethylxanthate, iron(III) ethylxanthate, iron(II) isopropylxanthate, iron(III) isopropylxanthate, iron(II) butylxanthate, iron(III) butylxanthate, iron(II) benzylxanthate, and iron(III) benzylxanthate.

Suitable iron β-diketonates include iron(II) acetylacetonate, iron(III) acetylacetonate, iron(II) trifluoroacetylacetonate, iron(III) trifluoroacetylacetonate, iron(II) hexafluoroacetylacetonate, iron(III) hexafluoroacetylacetonate, iron(II) benzoylacetonate, iron (III) benzoylacetonate, iron(II) 2,2,6,6-tetramethyl-3,5-heptanedionate, and iron(III) 2,2,6,6-tetramethyl-3,5-heptanedionate.

Suitable iron alkoxides or aryloxides include iron (II) methoxide, iron(III) methoxide, iron(II) ethoxide, iron(III) ethoxide, iron(II) isopropoxide, iron(III) isopropoxide, iron (II) 2-ethylhexoxide, iron(III) 2-ethylhexoxide, iron(II) phenoxide, iron(III) phenoxide, iron(II) nonylphenoxide, iron(III) nonylphenoxide, iron(II) naphthoxide, and iron(III) naphthoxide.

The term "organoiron compound" refers to any iron compound containing at least one covalent iron-carbon bond. Suitable organoiron compounds include bis (cyclopentadienyl)iron(II) (also called ferrocene), bis (pentamethylcyclopentadienyl)iron(II) (also called decamethylferrocene), bis(pentadienyl)iron(II), bis(2,4-dimethylpentadienyl)iron(II), bis(allyl)dicarbonyliron(II), (cyclopentadienyl) (pentadienyl)iron(II), tetra(1-norbornyl) iron(IV), (trimethylenemethane)tricarbonyliron(II), bis (butadiene) carbonyliron(0), butadienetricarbonyliron(0), and bis (cyclooctatetraene) iron(0).

The halogen-containing compound employed within ingredient (a) of the second embodiment may include various compounds or mixtures thereof that contain one or more halide ions. Examples of these halide ions include, but are not limited to, fluoride, chloride, bromide, and iodide. A combination of two or more of these halide ions can also be utilized. Halogen-containing compounds that are soluble in a hydrocarbon solvent are preferred. Hydrocarbon-insoluble halogen-containing compounds, however, can be suspended in the oligomerization medium to form the catalytically active species, and are therefore useful.

Suitable halogen-containing compounds include, but are not limited to, elemental halogens, mixed halogens, hydrogen halides, organic halides, inorganic halides, metallic halides, organometallic halides, and mixtures thereof. The preferred halogen-containing compounds are hydrogen halides, metallic halides, and organometallic halides, all of which contain at least one labile halide ion.

Suitable elemental halogens include fluorine, chlorine, bromine, and iodine. Some specific examples of suitable mixed halogens include iodine monochloride, iodine monobromide, iodine trichloride, and iodine pentafluoride.

Suitable hydrogen halides include hydrogen fluoride, hydrogen chloride, hydrogen bromide, and hydrogen iodide.

Suitable organic halides include t-butyl chloride, t-butyl bromides, allyl chloride, allyl bromide, benzyl chloride, benzyl bromide, chloro-di-phenylmethane, bromo-di-phenylmethane, triphenylmethyl chloride, triphenylmethyl bromide, benzylidene chloride, benzylidene bromide, methyltrichlorosilane, phenyltrichlorosilane, dimethyldichlorosilane, diphenyldichlorosilane, trimethylchlorosilane, benzoyl chloride, benzoyl bromide, propionyl chloride, propionyl bromide, methyl chloroformate, and methyl bromoformate.

Suitable inorganic halides include phosphorus trichloride, phosphorus tribromide, phosphorus pentachloride, phosphorus oxychloride, phosphorus oxybromide, boron trifluoride, boron trichloride, boron tribromide, silicon tetrafluoride, silicon tetrachloride, silicon tetrabromide, silicon tetraiodide, arsenic trichloride, arsenic tribromide, arsenic triiodide, selenium tetrachloride, selenium tetrabromide, tellurium tetrachloride, tellurium tetrabromide, and tellurium tetraiodide.

Suitable metallic halides include tin tetrachloride, tin tetrabromide, aluminum trichloride, aluminum tribromide, antimony trichloride, antimony pentachloride, antimony tribromide, aluminum triiodide, aluminum trifluoride, gallium trichloride, gallium tribromide, gallium triiodide, gallium trifluoride, indium trichloride, indium tribromide, indium triiodide, indium trifluoride, titanium tetrachloride, titanium tetrabromide, titanium tetraiodide, zinc dichloride, zinc dibromide, zinc diiodide, and zinc difluoride.

Suitable organometallic halides include dimethylaluminum chloride, diethylaluminum chloride, dimethylaluminum bromide, diethylaluminum bromide, dimethylaluminum fluoride, diethylaluminum fluoride, methylaluminum dichloride, ethylaluminum dichloride, methylaluminum dibromide, ethylaluminum dibromide, methylaluminum difluoride, ethylaluminum difluoride, methylaluminum sesquichloride, ethylaluminum sesquichloride, isobutylaluminum sesquichloride, methylmagnesium chloride, methylmagnesium bromide, methylmagnesium iodide, ethylmagnesium chloride, ethylmagnesium bromide, butylmagnesium chloride, butylmagnesium bromide, phenylmagnesium chloride, phenylmagnesium bromide, benzylmagnesium chloride, trimethyltin chloride, trimethyltin bromide, triethyltin chloride, triethyltin bromide, di-t-butyltin dichloride, di-t-butyltin dibromide, dibutyltin dichloride, dibutyltin dibromide, tributyltin chloride, and tributyltin bromide.

Useful silyl phosphonate compounds that can be employed as ingredient (b) of the catalyst composition include acyclic silyl phosphonates, cyclic silyl phosphonates, and mixtures thereof. Acyclic silyl phosphonates may be represented by the following structure:

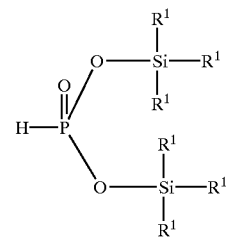

where each $R^1$, which may be the same or different, is a hydrogen atom or a mono-valent organic group. Preferably, each $R^1$ is a hydrocarbyl group such as, but not limited to, alkyl, cycloalkyl, substituted cycloalkyl, alkenyl, cycloalkenyl, substituted cycloalkenyl, aryl, substituted aryl, aralkyl, alkaryl, allyl, and alkynyl groups, with each group preferably containing from 1 carbon atom, or the appropriate minimum number of carbon atoms to form the group, up to about 20 carbon atoms. These hydrocarbyl groups may contain heteroatoms such as, but not limited to, nitrogen, oxygen, silicon, sulfur, and phosphorus atoms. The acyclic silyl phosphonates may be associated in dimeric, trimeric or oligomeric forms by hydrogen bonding.

Suitable acyclic silyl phosphonates include bis (trimethylsilyl) phosphonate, bis(dimethylsilyl) phosphonate, bis(triethylsilyl) phosphonate, bis(diethylsilyl) phosphonate, bis(tri-n-propylsilyl) phosphonate, bis(di-n-propylsilyl) phosphonate, bis(triisopropylsilyl) phosphonate, bis(diisopropylsilyl) phosphonate, bis(tri-n-butylsilyl) phosphonate, bis(di-n-butylsilyl) phosphonate, bis(triisobutylsilyl) phosphonate, bis(diisobutylsilyl)

phosphonate, bis(tri-t-butylsilyl) phosphonate, bis(di-t-butylsilyl) phosphonate, bis(trihexylsilyl) phosphonate, bis(dihexylsilyl) phosphonate, bis(trioctylsilyl) phosphonate, bis(dioctylsilyl) phosphonate, bis(tricyclohexylsilyl) phosphonate, bis(dicyclohexylsilyl) phosphonate, bis(triphenylsilyl) phosphonate, bis(diphenylsilyl) phosphonate, bis(tri-p-tol ylsilyl) phosphonate, bis(di-p-tolylsilyl) phosphonate, bis(tribenzylsilyl) phosphonate, bis(dibenzylsilyl) phosphonate, bis(methyldiethylsilyl) phosphonate, bis-p(methyldi-n-propylsilyl) phosphonate, bis(methyldi-n-propylsilyl) phosphonate, bis(methyldi-n-butylsilyl) phosphonate, bis(methyldiisobutylsilyl) phosphonate, bis(methyldi-t-butylsilyl) phosphonate, bis(methyldiphenylsilyl) phosphonate, bis(dimethylethylsilyl) phosphonate, bis(dimethyl-n-propylsilyl) phosphonate, bis(dimethylisopropylsilyl) phosphonate, bis(dimethyl-n-butylsilyl) phosphonate, bis(dimethylisobutylsilyl) phosphonate, bis(dimethyl-t-butylsilyl) phosphonate, bis(dimethylphenylsilyl) phosphonate, bis(t-butyldiphenylsilyl) phosphonate, bis[tris(2-ethylhexyl)silyl] phosphonate, bis[bis(2-ethylhexyl)silyl] phosphonate, bis[tris(nonylphenyl)silyl] phosphonate, bis[tris(2,4,6-trimethylphenyl)silyl] phosphonate, bis[bis(2,4,6-trimethylphenyl)silyl] phosphonate, bis[tris(4-fluorophenyl)silyl] phosphonate, bis[bis(4-fluorophenyl)silyl] phosphonate, bis[tris(pentafluorophenyl)silyl] phosphonate, bis[tris(trifluoromethyl)silyl] phosphonate, bis[tris(2,2,2-trifluoroethyl)silyl] phosphonate, bis[tris(trimethylsilyl)silyl] phosphonate, bis[tris(trimethylsilylmethyl)silyl] phosphonate, bis[tris(dimethylsilyl)silyl] phosphonate, bis[tris(2-butoxyethyl)silyl] phosphonate, bis(trimethoxysilyl) phosphonate, bis(triethoxysilyl) phosphonate, bis(triphenoxysilyl) phosphonate, bis[tris(trimethylsilyloxy)silyl] phosphonate, bis[tris(dimethylsilyloxy)silyl] phosphonate, and mixtures thereof.

Cyclic silyl phosphonates contain a ring structure that is formed by joining the two silicon atoms together or by bridging the two silicon atoms with one or more divalent organic groups. These cyclic silyl phosphonates may be represented by the following structure:

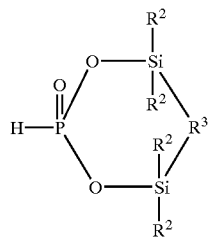

where each $R^2$, which may be the same or different, is a hydrogen atom or a mono-valent organic group, and $R^3$ is a bond between the silicon atoms or a divalent organic group. Bicyclic silyl phosphonates may be formed by joining two $R^2$ groups, and therefore the term cyclic silyl phosphonate will include multi-cyclic silyl phosphonates. Preferably, each $R^2$ is a hydrocarbyl group such as, but not limited to, alkyl, cycloalkyl, substituted cycloalkyl, alkenyl, cycloalkenyl, substituted cycloalkenyl, aryl, substituted aryl, aralkyl, alkaryl, allyl, and alkynyl groups, with each group preferably containing from 1 carbon atom, or the appropriate minimum number of carbon atoms to form the group, up to about 20 carbon atoms. These hydrocarbyl groups may contain heteroatoms such as, but not limited to, nitrogen, oxygen, silicon, sulfur, and phosphorus atoms. Preferably, $R^3$ is a hydrocarbylene group such as, but not limited to, alkylene, substituted alkylene, cycloalkylene, substituted cycloalkylene, alkenylene, substituted alkenylene, cycloalkenylene, substituted cycloalkenylene, arylene, and substituted arylene groups, with each group preferably containing from 1 carbon atom, or the appropriate minimum number of carbon atoms to form the group, up to about 20 carbon atoms. These hydrocarbylene groups may contain heteroatoms such as, but not limited to, nitrogen, oxygen, silicon, sulfur, and phosphorus atoms. The cyclic silyl phosphonates may be associated in dimeric, trimeric or oligomeric forms by hydrogen bonding.

Suitable cyclic silyl phosphonates include 2-oxo-(2H)-4,5-disila-1,3,2-dioxaphospholane, 2-oxo-(2H)-4,5-disila-4,4,5,5-tetramethyl-1,3,2-dioxaphospholane, 2-oxo-(2H)-4,5-disila-4,4,5,5-tetraethyl-1,3,2-dioxaphospholane, 2-oxo-(2H)-4,5-disila-4,4,5,5-tetraphenyl-1,3,2-dioxaphospholane, 2-oxo-(2H)-4,5-disila-4,4,5,5-tetrabenzyl-1,3,2-dioxaphospholane, 2-oxo-(2H)-4,5-disila-4,5-dimethyl-1,3,2-dioxaphospholane, 2-oxo-(2H)-4,5-disila-4,5-diethyl-1,3,2-dioxaphospholane, 2-oxo-(2H)-4,5-disila-4,5-diphenyl-1,3,2-dioxaphospholane, 2-oxo-(2H)-4,5-disila-4,5-dibenzyl-1,3,2-dioxaphospholane, 2-oxo-(2H)-4,5-disila-4-methyl-1,3,2-dioxaphospholane, 2-oxo-(2H)-4,6-disila-1,3,2-dioxaphosphorinane, 2-oxo-(2H)-4,6-disila-4,4,6,6-tetramethyl-1,3,2-dioxaphosphorinane, 2-oxo-(2H)-4,6-disila-4,4,6,6-tetraethyl-1,3,2-dioxaphosphorinane, 2-oxo-(2H)-4,6-disila-4,4,6,6-tetraphenyl-1,3,2-dioxaphosphorinane, 2-oxo-(2H)-4,6-disila-4,4,6,6-tetrabenzyl-1,3,2-dioxaphosphorinane, 2-oxo-(2H)-4,6-disila-4,6-dimethyl-1,3,2-dioxaphosphorinane, 2-oxo-(2H)-4,6-disila-4,6-diethyl-1,3,2-dioxaphosphorinane, 2-oxo-(2H)-4,6-disila-4,6-diphenyl-1,3,2-dioxaphosphorinane, 2-oxo-(2H)-4,6-disila-4,6-dibenzyl-1,3,2-dioxaphosphorinane, 2-oxo-(2H)-4,6-disila-5,5-dimethyl-1,3,2-dioxaphosphorinane, 2-oxo-(2H)-4,6-disila-5,5-diethyl-1,3,2-dioxaphosphorinane, 2-oxo-(2H)-4,6-disila-5,5-diphenyl-1,3,2-dioxaphosphorinane, 2-oxo-(2H)-4,6-disila-5,5-dibenzyl-1,3,2-dioxaphosphorinane, 2-oxo-(2H)-4,6-disila-5-ethyl-5-methyl-1,3,2-dioxaphosphorinane, 2-oxo-(2H)-4,6-disila-5-methyl-5-propyl-1,3,2-dioxaphosphorinane, 2-oxo-(2H)-4,6-disila-5-butyl-5-ethyl-1,3,2-dioxaphosphorinane, 2-oxo-(2H)-4,6-disila-4-isopropyl-5,5-dimethyl-1,3,2-dioxaphosphorinane, 2-oxo-(2H)-4,6-disila-4-propyl-5-ethyl-1,3,2-dioxaphosphorinane, 2-oxo-(2H)-4,6-disila-4-methyl-1,3,2-dioxaphosphorinane, and mixtures thereof.

Various organoaluminum compounds or mixtures thereof can be used as ingredient (c) of the catalyst composition. The term "organoaluminum compound" refers to any aluminum compound containing at least one covalent aluminum-carbon bond. Organoaluminum compounds that are soluble in a hydrocarbon solvent are preferred.

A preferred class of organoaluminum compounds is represented by the general formula $AlR_nX_{3-n}$, where each R, which may be the same or different, is a mono-valent organic group that is attached to the aluminum atom via a carbon atom, where each X, which may be the same or different, is a hydrogen atom, a carboxylate group, an alkoxide group, or an aryloxide group, and where n is an integer of 1 to 3. Preferably, each R is a hydrocarbyl group such as, but not limited to, alkyl, cycloalkyl, substituted cycloalkyl, alkenyl, cycloalkenyl, substituted cycloalkenyl, aryl, substituted aryl, aralkyl, alkaryl, allyl, and alkynyl groups, with each group preferably containing from 1 carbon atom, or the appropriate minimum number of carbon atoms to form the group, up to about 20 carbon atoms. These hydrocarbyl groups may contain heteroatoms such as, but not limited to, nitrogen, oxygen, silicon, sulfur, and phosphorus atoms. Preferably, each X is a carboxylate group, an alkoxide group, or an aryloxide group, with each group preferably containing from 1 carbon atom, or the appropriate minimum number of carbon atoms to form the group, up to about 20 carbon atoms.

Suitable organoaluminum compounds include, but are not limited to, trihydrocarbylaluminum, dihydrocarbylaluminum hydride, hydrocarbylaluminum dihydride, dihydrocarbylaluminum carboxylate, hydrocarbylaluminum bis(carboxylate), dihydrocarbylaluminum alkoxide, hydrocarbylaluminum dialkoxide, dihydrocarbylaluminum aryloxide, hydrocarbylaluminum diaryloxide, and the like, and mixtures thereof. Trihydrocarbylaluminum compounds are generally preferred.

Specific organoaluminum compounds include trimethylaluminum, triethylaluminum, triisobutylaluminum, tri-n-propylaluminum, triisopropylaluminum, tri-n-butylaluminum, tri-t-butylaluminum, tri-n-pentylaluminum, trineopentylaluminum, tri-n-hexylaluminum, tri-n-octylaluminum, tris(2-ethylhexyl)aluminum, tricyclohexylaluminum, tris(1-methylcyclopentyl)aluminum, triphenylaluminum, tri-p-tolylaluminum, tris(2,6-dimethylphenyl)aluminum, tribenzylaluminum, diethylphenylaluminum, diethyl-p-tolylaluminum, diethylbenzylaluminum, ethyldiphenylaluminum, ethyldi-p-tolylaluminum, ethyldibenzylaluminum, diethylaluminum hydride, di-n-propylaluminum hydride, diisopropylaluminum hydride, di-n-butylaluminum hydride, diisobutylaluminum hydride, di-n-octylaluminum hydride, diphenylaluminum hydride, di-p-tolylaluminum hydride, dibenzylaluminum hydride, phenylethylaluminum hydride, phenyl-n-propylaluminum hydride, phenylisopropylaluminum hydride, phenyl-n-butylaluminum hydride, phenylisobutylaluminum hydride, phenyl-n-octylaluminum hydride, p-tolylethylaluminum hydride, p-tolyl-n-propylaluminum hydride, p-tolylisopropylaluminum hydride, p-tolyl-n-butylaluminum hydride, p-tolylisobutylaluminum hydride, p-tolyl-n-octylaluminum hydride, benzylethylaluminum hydride, benzyl-n-propylaluminum hydride, benzylisopropylaluminum hydride, benzyl-n-butylaluminum hydride, benzylisobutylaluminum hydride, and benzyl-n-octylaluminum hydride, ethylaluminum dihydride, n-propylaluminum dihydride, isopropylaluminum dihydride, n-butylaluminum dihydride, isobutylaluminum dihydride, n-octylaluminum dihydride, dimethylaluminum hexanoate, diethylaluminum octoate, diisobutylaluminum 2-ethylhexanoate, dimethylaluminum neodecanoate, diethylaluminum stearate, diisobutylaluminum oleate, methylaluminum bis(hexanoate), ethylaluminum bis(octoate), isobutylaluminum bis(2-ethylhexanoate), methylaluminum bis(neodecanoate), ethylaluminum bis(stearate), isobutylaluminum bis(oleate), dimethylaluminum methoxide, diethylaluminum methoxide, diisobutylaluminum methoxide, dimethylaluminum ethoxide, diethylaluminum ethoxide, diisobutylaluminum ethoxide, dimethylaluminum phenoxide, diethylaluminum phenoxide, diisobutylaluminum phenoxide, methylaluminum dimethoxide, ethylaluminum dimethoxide, isobutylaluminum dimethoxide, methylaluminum diethoxide, ethylaluminum diethoxide, isobutylaluminum diethoxide, methylaluminum diphenoxide, ethylaluminum diphenoxide, isobutylaluminum diphenoxide, and the like, and mixtures thereof.

Another class of organoaluminum compounds is aluminoxanes. Aluminoxanes are known in the art and comprise oligomeric linear aluminoxanes that can be represented by the general formula:

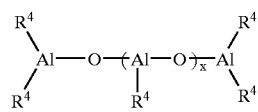

and oligomeric cyclic aluminoxanes that can be represented by the general formula:

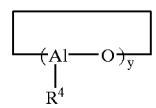

where x is an integer of 1 to about 100, preferably about 10 to about 50; y is an integer of 2 to about 100, preferably about 3 to about 20; where each $R^4$, which may be the same or different, is a mono-valent organic group that is attached to the aluminum atom via a carbon atom. Preferably, each $R^4$ is a hydrocarbyl group such as, but not limited to, alkyl, cycloalkyl, substituted cycloalkyl, alkenyl, cycloalkenyl, substituted cycloalkenyl, aryl, substituted aryl, aralkyl, alkaryl, allyl, and alkynyl groups, with each group preferably containing from 1 carbon atom, or the appropriate minimum number of carbon atoms to form the group, up to about 20 carbon atoms. These hydrocarbyl groups may contain heteroatoms such as, but not limited to, nitrogen, oxygen, silicon, sulfur, and phosphorus atoms. It should be noted that the number of moles of the aluminoxane as used in this application refers to the number of moles of the aluminum atoms rather than the number of moles of the oligomeric aluminoxane molecules. This convention is commonly employed in the art of catalysis utilizing aluminoxanes.

Aluminoxanes can be prepared by reacting trihydrocarbylaluminum compounds with water. This reaction can be performed according to known methods, such as (1) a method in which the trihydrocarbylaluminum compound is dissolved in an organic solvent and then contacted with water, (2) a method in which the trihydrocarbylaluminum compound is reacted with water of crystallization contained in, for example, metal salts, or water adsorbed in inorganic or organic compounds, and (3) a method in which the trihydrocarbylaluminum compound is reacted with water in the presence of the monomer or monomer solution that is to be polymerized.

Suitable aluminoxane compounds include methylaluminoxane (MAO), modified methylaluminoxane (MMAO), ethylaluminoxane, n-propylaluminoxane, isopropylaluminoxane, butylaluminoxane, isobutylaluminoxane, n-pentylaluminoxane, neopentylaluminoxane, n-hexylaluminoxane, n-octylaluminoxane, 2-ethylhexylaluminoxane, cylcohexylaluminoxane, 1-methylcyclopentylaluminoxane, phenylaluminoxane, 2,6-dimethylphenylaluminoxane, and the like, and mixtures thereof. Isobutylaluminoxane is particularly useful on the grounds of its availability and its solubility in aliphatic and cycloaliphatic hydrocarbon solvents. Modified methylaluminoxane can be formed by substituting about 20–80% of the methyl groups of methylaluminoxane with $C_2$ to $C_{12}$ hydrocarbyl groups, preferably with isobutyl groups, by using techniques known to those skilled in the art.

The catalyst composition of the present invention has very high catalytic activity for oligomerizing conjugated dienes over a wide range of total catalyst concentrations and catalyst ingredient ratios. The oligomerization products having the most desirable properties, however, are obtained within a narrower range of total catalyst concentrations and catalyst ingredient ratios. Further, it is believed that the three catalyst ingredients (a), (b), and (c) may interact to form an active catalyst species. Accordingly, the optimum concentration for any one catalyst ingredient is dependent upon the concentrations of the other three catalyst ingredients.

In the first embodiment, where the catalyst composition includes (a) a halogen-containing iron compound, (b) a silyl phosphonate, and (c) an organoaluminum compound, the molar ratio of the silyl phosphonate to the halogen-containing iron compound (P/Fe) can be varied from about 0.5:1 to about 50:1, more preferably from about 1:1 to about 25:1, and even more preferably from about 2:1 to about 10:1. And, the molar ratio of the organoaluminum compound to the iron-containing compound (Al/Fe) can be varied from about 1:1 to about 200:1, more preferably from about 2:1 to about 100:1, and even more preferably from about 3:1 to about 50:1.

In the second embodiment, where the catalyst composition includes (a) an iron-containing compound and a halogen-containing compound, (b) a silyl phosphonate, and (c) an organoaluminum compound, the molar ratio of the silyl phosphonate to the iron-containing compound (P/Fe) can be varied from about 0.5:1 to about 50:1, more preferably from about 1:1 to about 25:1, and even more preferably from about 2:1 to about 10:1. The molar ratio of the halogen-containing compound to the iron-containing compound (halogen/Fe) can be varied from about 0.5:1 to about 20:1, more preferably from about 1:1 to about 10:1, and even more preferably from about 2:1 to about 6:1. And, the molar ratio of the organoaluminum compound to the iron-containing compound (Al/Fe) can be varied from about 1:1 to about 200:1, more preferably from about 2:1 to about 100:1, and even more preferably from about 3:1 to about 50:1.

The catalyst composition is formed by combining or mixing the catalyst ingredients (a), (b), and (c). Although an active catalyst species is believed to result from this combination, the degree of interaction or reaction between the various ingredients or components is not known with any great degree of certainty. Therefore, the term "catalyst composition" encompasses a simple mixture of the ingredients, a complex of the various ingredients that is caused by physical or chemical forces of attraction, a chemical reaction product of the ingredients, or a combination of the foregoing.

The catalyst composition may be formed in situ by adding the catalyst ingredients to a solution containing monomer and solvent, or simply bulk monomer, in either a stepwise or simultaneous manner. When adding the catalyst ingredients in a stepwise manner, the order in which the ingredients are added is not critical. In the first embodiment, it is preferred to add the halogen-containing iron compound followed by the silyl phosphonate, and finally followed by the organoaluminum compound. In the second embodiment, it is preferred to add the iron-containing compound first, followed by the silyl phosphonate, then followed by the halogen-containing compound, and finally followed by the organoaluminum compound.

Second, the catalyst ingredients may be pre-mixed outside the oligomerization system at an appropriate temperature, which is generally from about −20° C. to about 80° C., and the resulting catalyst composition is then added to the monomer solution.

Third, the catalyst composition may be pre-formed in the presence of monomer. That is, the catalyst ingredients are pre-mixed in the presence of a small amount of the conjugated diene monomer at an appropriate temperature, which is generally from about −20° C. to about 80° C. The amount of the conjugated diene monomer that is used for pre-forming the catalyst can range from about 1 to about 500 moles per mole of the iron-containing compound or halogen-containing iron compound, more preferably from about 5 to about 250 moles, and even more preferably from about 10 to about 100 moles per mole of the iron-containing compound or halogen-containing iron compound. The resulting catalyst composition is then added to the remainder of the monomer that is to be oligomerized.

Fourth, the catalyst composition can be formed by using a two-stage procedure. The first stage involves reacting the iron-containing compound or halogen-containing iron compound with the organoaluminum compound in the presence of a small amount of the conjugated diene monomer at an appropriate temperature, which is generally from about −20° C. to about 80° C. In the second stage, the foregoing reaction mixture, the silyl phosphonate, and where appropriate the halogen-containing compound are charged in either a stepwise or simultaneous manner to the remainder of the monomer that is to be oligomerized.

Fifth, and most preferably, an iron-ligand complex is first formed by pre-combining the iron-containing compound or the halogen-containing iron compound with the silyl phosphonate. Once formed, this iron-ligand complex is combined with the organoaluminum compound, and where appropriate the halogen-containing compound, to form the active catalyst species. The iron-ligand complex can be formed separately or in the presence of the conjugated diene monomer that is to be oligomerized. This complexation reaction can be conducted at any convenient temperature at normal pressure, but for an increased rate of reaction, it is preferred to perform this reaction at room temperature or above. The time required for the formation of the iron-ligand complex is usually within the range of about 10 minutes to about 2 hours after mixing the iron-containing or halogen-containing iron compound with the silyl phosphonate. The temperature and time used for the formation of the iron-ligand complex will depend upon several variables including the particular starting materials and the solvent employed. Once formed, the iron-ligand complex can be used without isolation from the complexation reaction mixture. If desired, however, the iron-ligand complex may be isolated from the complexation reaction mixture before use.

When a solution of the catalyst composition or one or more of the catalyst ingredients is prepared outside the oligomerization system as set forth in the foregoing methods, an organic solvent or carrier is preferably employed. The organic solvent may serve to dissolve the catalyst composition or ingredients, or the solvent may simply serve as a carrier in which the catalyst composition or ingredients may be suspended. Desirably, an organic solvent that is inert with respect to the catalyst composition is used. Useful solvents include hydrocarbon solvents such as aromatic hydrocarbons, aliphatic hydrocarbons, and cycloaliphatic hydrocarbons. Non-limiting examples of aromatic hydrocarbon solvents include benzene, toluene, xylenes, ethylbenzene, diethylbenzene, mesitylene, and the like. Non-limiting examples of aliphatic hydrocarbon solvents include n-pentane, n-hexane, n-heptane, n-octane, n-nonane, n-decane, isopentane, isohexanes, isopentanes, isooctanes, 2,2-dimethylbutane, petroleum ether, kerosene, petroleum spirits, and the like. And, non-limiting examples of cycloaliphatic hydrocarbon solvents include cyclopentane, cyclohexane, methylcyclopentane, methylcyclohexane, and the like. Commercial mixtures of the above hydrocarbons may also be used. For environmental reasons, aliphatic and cycloaliphatic solvents are highly preferred.

The catalyst composition of this invention exhibits very high catalytic activity for the oligomerization of conjugated dienes. Some specific examples of suitable conjugated diene monomers that can be oligomerized by means of the catalyst composition of this invention include 1,3-butadiene, isoprene, 1,3-pentadiene, 1,3-hexadiene, 2,3-dimethyl-1,3-butadiene, 2-ethyl-1,3-butadiene, 2-methyl-1,3-pentadiene, 3-methyl-1,3-pentadiene, 4-methyl-1,3-pentadiene, and 2,4-hexadiene. The preferred monomers are 1,3-butadiene, isoprene, 1,3-pentadiene, and 1,3-hexadiene. Mixtures of two or more conjugated diene monomers may also be utilized in co-oligomerization.

The production of conjugated diene oligomers is accomplished by oligomerizing conjugated diene monomers in the presence of a catalytically effective amount of the foregoing catalyst composition. The total catalyst concentration to be employed in the oligomerization mass depends on the interplay of various factors such as the purity of the ingredients, the oligomerization rate and conversion desired, the oligomerization temperature, and many other factors. Accordingly, specific total catalyst concentrations cannot be definitively set forth except to say that catalytically effective amounts of the respective catalyst ingredients should be used. Generally, the amount of the iron-containing compound or halogen-containing iron compound used can be varied from about 0.01 to about 2 mmol per 100 g of the conjugated diene monomer, with a more preferred range being from about 0.02 to about 1.0 mmol per 100 g of the conjugated diene monomer, and a most preferred range being from about 0.05 to about 0.5 mmol per 100 g of the conjugated diene monomer.

The oligomerization of conjugated dienes is preferably carried out in an organic solvent as the diluent. That is, an amount of the organic solvent in addition to the organic solvent that may be used in preparing the catalyst composition is added to the oligomerization system. The additional organic solvent may be either the same as or different from the organic solvent contained in the catalyst solutions. Preferably, an organic solvent that is inert with respect to the catalyst composition employed to catalyze the oligomerization reaction is selected. Exemplary hydrocarbon solvents have been set forth above.

The concentration of the conjugated diene monomer to be oligomerized is not limited to a special range. Preferably, however, the concentration of the conjugated diene monomer present in the oligomerization medium at the beginning of the oligomerization is in a range of from about 3% to about 80% by weight, more preferably from about 5% to about 50% by weight, and even more preferably from about 10% to about 30% by weight.

The oligomerization of conjugated dienes may also be carried out by means of bulk oligomerization, which refers to a reaction environment where no solvents are employed. Bulk oligomerization can be conducted either in a condensed liquid phase or in a gas phase.

The oligomerization of conjugated dienes may be carried out as a batch process, continuous process, or even semi-continuous process. In the semi-continuous process, conjugated diene monomer is intermittently charged as needed to replace that monomer already oligomerized. In any case, the oligomerization is desirably conducted under anaerobic conditions by using an inert protective gas such as nitrogen, argon or helium, with moderate to vigorous agitation. The oligomerization temperature employed may vary widely from a low temperature, such as $-10°$ C. or below, to a high temperature such as $100°$ C. or above, with a preferred temperature range being from about $20°$ C. to about $90°$ C. In general, elevated temperatures are undesirable due to thermal polymerization of the oligomers. The heat of oligomerization may be removed by external cooling, cooling by evaporation of the conjugated diene monomer or the solvent, or a combination of the two methods. Although the pressure employed in the practice of this invention also may vary widely, a preferred pressure range is from about 1 atmosphere to about 10 atmospheres.

The reaction time for the oligomerization process of this invention can vary widely but will generally be from a few minutes, e.g., 5 minutes, to a few hours, e.g., 8 hours, depending upon such factors as the type of conjugated diene, the temperature, the catalyst concentration, the catalyst ingredient ratio, and the conversion desired. In general, due to the very high catalytic activity of the catalyst composition of this invention, the reaction time is quite short even with the use of very low catalyst levels. Therefore, high conversion and high productivity in terms of pounds of product per pound of catalyst per hour are realized. Furthermore, since the catalyst composition of this invention is highly active even at low temperatures, the oligomerization of conjugated dienes may be carried out under very mild temperature conditions, thereby minimizing the formation of undesirable by-products.

Once a desired conversion is achieved, the oligomerization reaction can be stopped by adding a terminator that inactivates the catalyst. Typically, the terminator employed is a protic compound, which includes, but is not limited to, an alcohol, a carboxylic acid, an inorganic acid, water, or a combination thereof. A stabilizer such as 2,6-di-tert-butyl-4-methylphenol may be added along with, before or after addition of the terminator. The amount of the stabilizer employed is usually in the range of 0.01% to 0.1% by weight of the oligomerization product. When the oligomerization reaction has been stopped, the products can be recovered from the reaction mixture by conventional techniques such as fractional distillation and preparative chromatography which are well known to those skilled in the art.

In order to demonstrate the practice the present invention, the following examples have been prepared and tested as described. The examples should not, however, be viewed as limiting the scope of the invention. The claims will serve to define the invention.

EXAMPLES

Example 1

Bis(trimethylsilyl) phosphonate (formula: $HP(O)(OSiMe_3)_2$) was synthesized by reacting anhydrous phosphorous acid ($H_3PO_3$) with hexamethyldisiloxane ($Me_3SiOSiMe_3$) in the presence of anhydrous zinc chloride as the catalyst.

Anhydrous phosphorous acid (33.1 g, 0.404 mol), hexamethyldisiloxane (98.4 g, 0.606 mol), anhydrous zinc chloride (2.0 g, 0.015 mol), and benzene (240 mL) were mixed in a round-bottom reaction flask which was connected to a Dean-Stark trap and a reflux condenser. The mixture was heated to reflux for 24 hours, with continuous removal of water via the Dean-Stark trap. The reaction flask was then connected to a distillation head and a receiving flask. The benzene solvent and the unreacted hexamethyldisiloxane were removed by distillation at atmospheric pressure. The remaining crude product was distilled under vacuum, yielding bis(trimethylsilyl) phosphonate as a colorless liquid (51.7 g, 0.228 mol, 57% yield). The identity of the product was established by nuclear magnetic resonance (NMR) spectroscopy. $^1$H NMR data (CDCl$_3$, 25° C., referenced to tetramethylsilane): δ6.85 (doublet, $^1J_{HP=}$699 Hz, 1 H, H-P), 0.31 (singlet, 18 H, CH$_3$). $^{13}$P NMR data (CDCl$_3$, 25° C., referenced to external 85% H$_3$PO$_4$): δ−14.2 (doublet, $^1J_{HP=}$698 Hz).

Example 2

Inside a glovebox operated under an argon atmosphere, an oven-dried 7-oz. glass bottle was charged with 228 mg (1.80 mmol) of anhydrous iron(II) chloride powder and 1.63 g (7.20 mmol) of bis(trimethylsilyl) phosphonate. The bottle was capped with a self-sealing rubber liner and a perforated metal cap, and then the bottle was removed from the glovebox. Toluene (27.6 mL) was charged into the bottle. The bottle was shaken at room temperature for 2 hour, resulting in the dissolution of the iron(II) chloride solid and the formation of a pale-yellow solution containing the complex of iron(II) chloride with bis(trimethylsilyl) phosphonate ligand. The concentration of the iron-ligand complex in the solution was calculated to be 0.0614 mmol per mL.

Example 3

Inside a glovebox operated under an argon atmosphere, an oven-dried 7-oz. glass bottle was charged with 292 mg (1.80 mmol) of anhydrous iron(III) chloride powder and 1.63 g (7.20 mmol) of bis(trimethylsilyl) phosphonate. The bottle was capped with a self-sealing rubber liner and a perforated metal cap, and then the bottle was removed from the glovebox. Toluene (30.4 mL) was charged into the bottle. The bottle was shaken at room temperature for 5 minutes, resulting in the dissolution of the iron(III) chloride solid and the formation of a yellow solution containing the complex of iron (III) chloride with bis (trimethylsilyl) phosphonate ligand. The concentration of the iron-ligand complex in the solution was calculated to be 0.0559 mmol per mL.

Example 4

Inside a glovebox operated under an argon atmosphere, an oven-dried 7-oz. glass bottle was charged with 388 mg (1.80 mmol) of anhydrous iron(II) bromide powder and 1.63 g (7.20 mmol) of bis(trimethylsilyl) phosphonate. The bottle was capped with a self-sealing rubber liner and a perforated metal cap, and then the bottle was removed from the glovebox. Toluene (27.5 mL) was charged into the bottle. The bottle was tumbled for 10 hours in a water bath maintained at 80° C., resulting in the dissolution of the iron(II) bromide solid and the formation of an orange solution containing the complex of iron(II) bromide with bis(trimethylsilyl) phosphonate ligand. The concentration of the iron-ligand complex in the solution was calculated to be 0.0615 mmol per mL.

Example 5

Inside a glovebox operated under an argon atmosphere, an oven-dried 7-oz. glass bottle was charged with 532 mg (1.80 mmol) of anhydrous iron(III) bromide powder and 1.63 g (7.20 mmol) of bis(trimethylsilyl) phosphonate. The bottle was capped with a self-sealing rubber liner and a perforated metal cap, and then the bottle was removed from the glovebox. Toluene (29.6 mL) was charged into the bottle. The bottle was shaken at room temperature for 10 minutes, resulting in the dissolution of the iron(III) bromide solid and the formation of a deep-red solution containing the complex of iron(III) bromide with bis(trimethylsilyl) phosphonate ligand. The concentration of the iron-ligand complex in the solution was calculated to be 0.0575 mmol per mL.

Example 6

An oven-dried 1-liter glass bottle was capped with a self-sealing rubber liner and a perforated metal cap. After the bottle was thoroughly purged with a stream of dry nitrogen, the bottle was charged with 230.4 g of a 1,3-butadiene/hexanes blend containing 21.7% of 1,3-butadiene, followed by 0.45 mmol of triisobutylaluminum and 0.050 mmol of the complex of iron(II) chloride with bis(trimethylsilyl) phosphonate ligand as prepared in Example 2. The bottle was placed in a water bath maintained at room temperature. After 6 hours, the oligomerization was terminated by addition of 0.30 mL of isopropanol. The analysis of the resulting oligomerization mixture by using gas chromatography/mass spectrometry (GC/MS) indicated that 99.9% of the 1,3-butadiene monomer used had been converted, the product being a mixture of 5-methyl-1,3,6-heptatriene (90.5%) and 1,3,6-octatriene (9.5%). The experimental data are summnnarized in Table I.

TABLE I

| Example No. | 6 | 7 | 8 | 9 |
|---|---|---|---|---|
| 21.7% 1,3-Bd/hexanes (g) | 230.4 | 230.4 | 230.4 | 230.4 |
| i-Bu$_3$Al (mmol) | 0.45 | 0.50 | 0.55 | 0.60 |
| FeCl$_2${HP(O)(OSiMe$_3$)$_2$}$_4$ (mmol) | 0.050 | 0.050 | 0.050 | 0.050 |
| Fe/Al molar ratio | 1:9 | 1:10 | 1:11 | 1:12 |
| Conversion (%) after 6 hr | 99.9 | 99.8 | 100 | 100 |
| Oligomerization product composition: | | | | |
| S-Methyl-1,3,6-heptatriene (%) | 90.5 | 90.4 | 90.4 | 90.6 |
| 1,3,6-Octatriene (%) | 9.5 | 9.6 | 9.6 | 9.4 |

Examples 7–9

In Examples 7–9, the procedure in Example 6 was repeated except that the catalyst ingredient ratio was varied as shown in Table I. The monomer charge, the amounts of the catalyst ingredients, and the oligomerization product composition are summarized in Table I.

Examples 10–13

In Examples 10–13, the procedure in Example 6 was repeated except that the complex of iron(III) chloride with bis(trimethylsilyl) phosphonate ligand as prepared in Example 3 was substituted for the complex of iron(II) chloride with bis(trimethylsilyl) phosphonate ligand as prepared in Example 2. The monomer charge, the amounts of the catalyst ingredients, and the oligomerization product composition are summarized in Table II.

TABLE II

| Example No. | 10 | 11 | 12 | 13 |
|---|---|---|---|---|
| 21.7% 1,3-Bd/hexanes (g) | 230.4 | 230.4 | 230.4 | 230.4 |
| i-Bu$_3$Al (mmol) | 0.45 | 0.50 | 0.55 | 0.60 |

TABLE II-continued

| Example No. | 10 | 11 | 12 | 13 |
|---|---|---|---|---|
| FeCl$_3${HP(O)(OSiMe$_3$)$_2$}$_4$ (mmol) | 0.050 | 0.050 | 0.050 | 0.050 |
| Fe/Al molar ratio | 1:9 | 1:10 | 1:11 | 1:12 |
| Conversion (%) after 6 hr | 100 | 100 | 99.9 | 100 |
| Oligomerization product composition: | | | | |
| 5-Methyl-1,3,6-heptatriene (%) | 90.3 | 90.4 | 90.4 | 90.4 |
| 1,3,6-Octatriene (%) | 9.7 | 9.5 | 9.6 | 9.6 |

Examples 14–17

In Examples 14–17, the procedure in Example 6 was repeated except that the complex of iron(II) bromide with bis(trimethylsilyl) phosphonate ligand as prepared in Example 4 was substituted for the complex of iron(II) chloride with bis(trimethylsilyl) phosphonate ligand as prepared in Example 2. The monomer charge, the amounts of the catalyst ingredients, and the oligomerization product composition are summarized in Table III.

TABLE III

| Example No. | 14 | 15 | 16 | 17 |
|---|---|---|---|---|
| 21.7% 1,3-Bd/hexanes (g) | 230.4 | 230.4 | 230.4 | 230.4 |
| i-Bu$_3$Al (mmol) | 0.45 | 0.50 | 0.55 | 0.60 |
| FeBr$_2${HP(O)(OSiMe$_3$)$_2$}$_4$ (mmol) | 0.050 | 0.050 | 0.050 | 0.050 |
| Fe/Al molar ratio | 1:9 | 1:10 | 1:11 | 1:12 |
| Conversion (%) after 6 hr | 99.4 | 99.5 | 99.6 | 99.6 |
| Oligomerization product composition: | | | | |
| 5-Methyl-1,3,6-heptatriene (%) | 92.1 | 91.8 | 92.1 | 92.1 |
| 1,3,6-Octatriene (%) | 7.9 | 8.2 | 7.9 | 7.9 |

Examples 18–21

In Examples 18–21, the procedure in Example 6 was repeated except that the complex of iron(III) bromide with bis(trimethylsilyl) phosphonate ligand as prepared in Example 5 was substituted for the complex of iron(II) chloride with bis(trimethylsilyl) phosphonate ligand as prepared in Example 2. The monomer charge, the amounts of the catalyst ingredients, and the oligomerization product composition are summarized in Table IV.

TABLE IV

| Example No. | 18 | 19 | 20 | 21 |
|---|---|---|---|---|
| 21.7% 1,3-Bd/hexanes (g) | 230.4 | 230.4 | 230.4 | 230.4 |
| i-BU$_3$Al (mmol) | 0.45 | 0.50 | 0.55 | 0.60 |
| FeBr$_3${HP(O)(OSiMe$_3$)$_2$}$_4$ (mmol) | 0.050 | 0.050 | 0.050 | 0.050 |
| Fe/Al molar ratio | 1:9 | 1:10 | 1:11 | 1:12 |
| Conversion (%) after 6 hr | 99.1 | 99.3 | 99.4 | 99.4 |
| Oligomerization product composition: | | | | |
| 5-Methyl-1,3,6-heptatriene (%) | 92.4 | 92.2 | 92.1 | 92.0 |
| 1,3,6-Octatriene (%) | 7.6 | 7.8 | 7.9 | 8.0 |

The results described in Examples 6–21 show that at mild temperature conditions, 1,3-butadiene can be converted substantially quantitatively to the two acyclic dimers with a selectivity of 100% by utilizing the catalyst composition of the present invention.

Example 22

An oven-dried 1-liter glass bottle was capped with a self-sealing rubber liner and a perforated metal cap. After the bottle was thoroughly purged with a stream of dry nitrogen, the bottle was charged with 230.4 g of a 1,3-butadiene/hexanes blend containing 21.7% by weight of 1,3-butadiene. The following catalyst ingredients were then charged into the bottle in the following order: (1) 0.050 mmol of iron(III) 2-ethylhexanoate, (2) 0.20 mmol of bis(trimethylsilyl) phosphonate, (3) 0.15 mmol of diisobutylaluminum chloride, and (4) 0.25 mmol of triisobutylaluminum. The bottle was placed in a water bath maintained at room temperature. After 7 hours, the oligomerization was terminated by addition of 0.30 mL of isopropanol. The analysis of the resulting oligomerization mixture by using gas chromatography/mass spectrometry (GC/MS) indicated that 98.9% of the 1,3-butadiene monomer used had been converted, the product being a mixture of 5-methyl-1,3,6-heptatriene (90.9%) and 1,3,6-octatriene (9.1%). The experimental data are summarized in Table V.

TABLE V

| Example No. | 22 | 23 | 24 | 25 | 26 |
|---|---|---|---|---|---|
| 21.7% 1,3-Bd/hexanes (g) | 230.4 | 230.4 | 230.4 | 230.4 | 230.4 |
| Fe(2-EHA)$_3$ (mmol) | 0.050 | 0.050 | 0.050 | 0.050 | 0.050 |
| HP(O)(OSiMe$_3$)$_2$ (mmol) | 0.20 | 0.20 | 0.20 | 0.20 | 0.20 |
| i-Bu$_2$AlCl (mmol) | 0.15 | 0.15 | 0.15 | 0.15 | 0.15 |
| i-Bu$_3$Al (mmol) | 0.25 | 0.30 | 0.35 | 0.40 | 0.45 |
| Fe/P/Cl/Al molar ratio | 1:4:3:5 | 1:4:3:6 | 1:4:3:7 | 1:4:3:8 | 1:4:3:9 |
| Conversion (%) after 7 hr | 98.9 | 99.6 | 99.9 | 99.9 | 99.9 |
| Oligomerization product composition: | | | | | |
| 5-Methyl-1,3,6-heptatriene (%) | 90.9 | 90.1 | 89.9 | 89.9 | 89.7 |
| 1,3,6-Octatriene (%) | 9.1 | 9.9 | 10.1 | 10.1 | 10.3 |

Example 23–26

In Examples 23–26, the procedure in Example 22 was repeated except that the catalyst ingredient ratio was varied as shown in Table V. The monomer charge, the amounts of the catalyst ingredients, and the oligomerization product composition are summarized in Table V.

The results described in Examples 22–26 show that at mild temperature conditions, 1,3-butadiene can be converted substantially quantitatively to the two acyclic dimers with a selectivity of 100% by utilizing the catalyst composition of the present invention.

Various modifications and alterations that do not depart from the scope and spirit of this invention will become apparent to those skilled in the art. This invention is not to be duly limited to the illustrative embodiments set forth herein.

What is claimed is:

1. A catalyst composition that is the combination of or the reaction product of ingredients comprising:
   (a) (i) a halogen-containing iron compound or (ii) an iron-containing compound and a halogen-containing compound;
   (b) a silyl phosphonate; and
   (c) an organoaluminum compound.

2. The catalyst composition of claim 1, where said halogen-containing iron compound is an iron fluoride, iron chloride, iron bromide, iron iodide, iron oxyhalide, or a mixture thereof.

3. The catalyst composition of claim 1, where said iron-containing compound is an iron carboxylate, iron organophosphate, iron organophosphonate, iron organophosphinate, iron carbamate, iron dithiocarbamate, iron xanthate, iron β-diketonate, iron alkoxide, iron aryloxide, organoiron compound, or mixture thereof.

4. The catalyst composition of claim 1, where said halogen-containing compound is elemental halogen, mixed halogen, hydrogen halide, organic halide, inorganic halide, metallic halide, organometallic halide, or a mixture thereof.

5. The catalyst composition of claim 1, where said silyl phosphonate is an acyclic silyl phosphonate defined by the following structure:

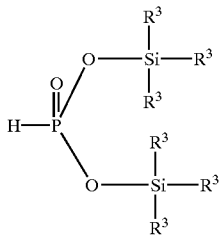

where each $R^1$, which may be the same or different, is a hydrogen atom or a mono-valent organic group.

6. The catalyst composition of claim 5, where $R^1$ is an alkyl, cycloalkyl, substituted cycloalkyl, alkenyl, cycloalkenyl, substituted cycloalkenyl, aryl, substituted aryl, aralkyl, alkaryl, allyl, or alkynyl group.

7. The catalyst composition of claim 6, where said acyclic silyl phosphonate is bis(trimethylsilyl) phosphonate, bis(triethylsilyl) phosphonate, bis(tri-n-propylsilyl) phosphonate, bis(triisopropylsilyl) phosphonate, bis(tri-n-butylsilyl) phosphonate, bis(tricyclohexylsilyl) phosphonate, bis(triphenylsilyl) phosphonate, bis[tris(2-ethylhexyl)silyl] phosphonate, or bis[tris(2,4,6-trimethylphenyl)silyl] phosphonate.

8. The catalyst composition of claim 1, where said silyl phosphonate is a cyclic silyl phosphonate that is defined by the following structure:

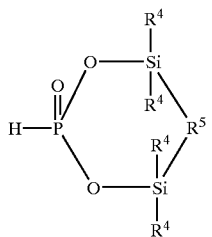

where each $R^2$, which may be the same or different, is a hydrogen atom or a mono-valent organic group, and $R^3$ is a bond between silicon atoms or a divalent organic group.

9. The catalyst composition of claim 8, where $R^4$ is an alkyl, cycloalkyl, substituted cycloalkyl, alkenyl, cycloalkenyl, substituted cycloalkenyl, aryl, substituted aryl, aralkyl, alkaryl, allyl, or alkynyl group, and where $R^5$ is an alkylene, substituted alkylene, cycloalkylene, substituted cycloalkylene, alkenylene, substituted alkenylene, cycloalkenylene, substituted cycloalkenylene, arylene, or substituted arylene group.

10. The catalyst composition of claim 9, where said cyclic silyl phosphonate is 2-oxo-(2H)-4,5-disila-1,3,2-dioxaphospholane, 2-oxo-(2H)-4,5-disila-4,4,5,5-tetramethyl-1,3,2-dioxaphospholane, 2-oxo-(2H)-4,5-disila-4,4,5,5-tetraphenyl-1,3,2-dioxaphospholane, 2-oxo-(2H)-4,6-disila-1,3,2-dioxaphosphorinane, 2-oxo-(2H)-4,6-disila-4,4,6,6-tetramethyl-1,3,2-dioxaphosphorinane, 2-oxo-(2H)-4,6-disila-4,4,6,6-tetraethyl-1,3,2-dioxaphosphorinane, 2-oxo-(2H)-4,6-disila-4,4,6,6-tetraphenyl-1,3,2-dioxaphosphorinane, 2-oxo-(2H)-4,6-disila-4,4,6,6-tetrabenzyl-1,3,2-dioxaphosphorinane, 2-oxo-(2H)-4,6-disila-4,6-dimethyl-1,3,2-dioxaphosphorinane, or 2-oxo-(2H)-4,6-disila-4,6-diethyl-1,3,2-dioxaphosphorinane.

11. The catalyst composition of claim 1, where the organoaluminum compound is defined by the formula $AlR_nX_{3-n}$, where each R, which may be the same or different, is a mono-valent organic group that is attached to the aluminum atom via a carbon atom, where each X, which may be the same or different, is a hydrogen atom, a carboxylate group, an alkoxide group, or an aryloxide group, and where n is an integer of 1 to 3.

12. The catalyst composition of claim 11, where each R is an alkyl, cycloalkyl, substituted cycloalkyl, alkenyl, cycloalkenyl, substituted cycloalkenyl, aryl, substituted aryl, aralkyl, alkaryl, allyl, or alkynyl group.

13. The catalyst composition of claim 12, where said organoaluminum compound is trihydrocarbylaluminum, dihydrocarbylaluminum hydride, hydrocarbylaluminum dihydride, dihydrocarbylaluminum carboxylate, hydrocarbylaluminum bis(carboxylate), dihydrocarbylaluminum alkoxide, hydrocarbylaluminum dialkoxide, dihydrocarbylaluminum aryloxide, hydrocarbylaluminum diaryloxide or mixtures thereof.

14. The catalyst composition of claim 1, where said organoaluminum compound is an oligomeric linear aluminoxane, an oligomeric cyclic aluminoxane, or a mixture thereof, where the oligomeric linear aluminoxane is defined by the formula:

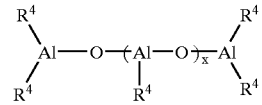

and the oligomeric cyclic aluminoxane is defined by the formula:

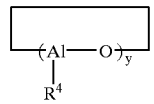

where x is an integer of 1 to about 100; y is an integer of 2 to about 100; where each $R^4$, which may be the same or different, is a mono-valent organic group that is attached to the aluminum atom via a carbon atom.

15. The catalyst composition of claim 14, where $R^4$ is an alkyl, cycloalkyl, substituted cycloalkyl, alkenyl, cycloalkenyl, substituted cycloalkenyl, aryl, substituted aryl, aralkyl, alkaryl, allyl, or alkynyl group.

16. The catalyst composition of claim 15, where said aluminoxane is methylaluminoxane, modified methylaluminoxane, ethylaluminoxane, n-propylaluminoxane, isobutylaluminoxane, or mixtures thereof.

17. The catalyst composition of claim 1, where the molar ratio of said organoaluminum compound to said halogen-containing iron compound or said iron-containing compound is from about 1:1 to about 200:1, and the molar ratio of said silyl phosphonate to said halogen-containing iron compound or said iron-containing compound is from about 0.5:1 to about 50:1.

18. The catalyst composition of claim 17, where the molar ratio of said organoaluminum compound to said halogen-containing iron compound or said iron-containing compound is from about 2:1 to about 100:1, and the molar ratio of the silyl phosphonate to said iron-containing compound is from about 1:1 to about 25:1.

19. A catalyst composition formed by a process comprising the steps of combining:

(a) (i) a halogen-containing iron compound or (ii) an iron-containing compound and a halogen-containing compound;

(b) a silyl phosphonate; and (c) an organoaluminum compound.

20. A process for forming conjugated diene oligomers comprising the step of:

oligomerizing conjugated diene monomers in the presence of a catalytically effective amount of a catalyst composition formed by combining:

(a) (i) a halogen-containing iron compound or (ii) an iron-containing compound and a halogen-containing compound;

(b) a silyl phosphonate; and (c) an organoaluminum compound.

* * * * *

UNITED STATES PATENT AND TRADEMARK OFFICE
CERTIFICATE OF CORRECTION

PATENT NO. : 6,433,237 B1
DATED : August 13, 2002
INVENTOR(S) : Steven Luo

It is certified that error appears in the above-identified patent and that said Letters Patent is hereby corrected as shown below:

Column 19,
Line 22, "where each $R^1$," should read -- where each $R^3$, --;
Line 24, "where each $R^1$," should read -- where each $R^3$, --;
Line 51, "where each $R^2$," should read -- where each $R^4$, --;
Line 52, "and $R^3$ is" should read -- and $R^5$ is --;
Line 54, "where R is a n" should read -- where $R^4$ is an --.

Signed and Sealed this

Thirtieth Day of March, 2004

JON W. DUDAS
*Acting Director of the United States Patent and Trademark Office*